US007488003B2

(12) United States Patent
Weisz et al.

(10) Patent No.: US 7,488,003 B2

(45) Date of Patent: Feb. 10, 2009

(54) LABEL SUPPLY, LABEL HANDLING METHOD AND LABEL PRINTING APPARATUS

(75) Inventors: Robert J. Weisz, Thornhill (CA); Nigel G. Mills, Kettering, OH (US); Kinred Bowling, Dayton, OH (US); Karl S. Schroeder, Clayton, OH (US)

(73) Assignee: Premark FEG L.L.C., Wilmington, DE (US)

( * ) Notice: Subject to any disclaimer, the term of this patent is extended or adjusted under 35 U.S.C. 154(b) by 80 days.

(21) Appl. No.: 11/393,606

(22) Filed: Mar. 30, 2006

(65) Prior Publication Data

US 2007/0252381 A1 Nov. 1, 2007

(51) Int. Cl.

| | |
|---|---|
| ***B42D 15/00*** | (2006.01) |
| ***A61F 13/15*** | (2006.01) |
| ***B41F 1/08*** | (2006.01) |

(52) U.S. Cl. ........................ 283/105; 283/81; 283/103; 156/227; 101/288

(58) Field of Classification Search ................ 428/40.1, 428/42.3, 43, 124; 156/204, 227; 283/81, 283/101, 103, 105, 56; 101/288

See application file for complete search history.

(56) References Cited

U.S. PATENT DOCUMENTS 2,420,045 A 5/1947 Krug
3,711,683 A 1/1973 Hamisch, Sr.
3,757,037 A 9/1973 Bialek
3,994,089 A 11/1976 Schwartz
4,323,608 A 4/1982 Denny et al.
4,423,486 A 12/1983 Berner
4,457,539 A 7/1984 Hamisch, Jr.
4,598,780 A 7/1986 Iwasaki et al.
4,674,041 A 6/1987 Lemon et al.
4,723,212 A 2/1988 Mindrum et al.
4,821,186 A 4/1989 Munakata et al.
4,901,237 A 2/1990 Hikita et al.
4,901,457 A 2/1990 Chandler
4,910,672 A 3/1990 Off et al.
4,928,229 A 5/1990 Teraoka et al.
4,929,818 A 5/1990 Bradbury et al.
4,932,485 A 6/1990 Mori
5,083,638 A 1/1992 Schneider
5,090,310 A * 2/1992 Motoe ........................ 101/114

(Continued)

FOREIGN PATENT DOCUMENTS

EP 0568088 A2 11/1993

(Continued)

OTHER PUBLICATIONS

Ishida, *AC-3000 Series* brochure, 6 pages, published at least as early as Nov. 26, 1996.

(Continued)

*Primary Examiner*—Dana Ross
*Assistant Examiner*—Kyle Grabowski
(74) *Attorney, Agent, or Firm*—Thompson Hine LLP

(57) ABSTRACT

A supply of labels may be configured to facilitate folding. A label handling method involves initiating a label fold prior to a label completely exiting a label exit opening. A label apparatus includes a label obstructing member to promote label folding.

15 Claims, 8 Drawing Sheets

U.S. PATENT DOCUMENTS

| | | | | |
|---|---|---|---|---|
| 5,172,936 | A | 12/1992 | Sullivan et al. | |
| 5,173,851 | A | 12/1992 | Off et al. | |
| 5,185,695 | A | 2/1993 | Pruchnicki | |
| 5,192,141 | A * | 3/1993 | Chung et al. | 400/56 |
| 5,200,889 | A | 4/1993 | Mori | |
| 5,329,713 | A | 7/1994 | Lundell | |
| 5,350,612 | A | 9/1994 | Stern et al. | |
| RE34,915 | E | 4/1995 | Nichtberger et al. | |
| 5,413,384 | A * | 5/1995 | Principe et al. | 283/81 |
| 5,439,721 | A | 8/1995 | Pedroli et al. | |
| 5,560,718 | A | 10/1996 | Furuya | |
| 5,578,797 | A | 11/1996 | Hewitt et al. | |
| 5,612,868 | A | 3/1997 | Off et al. | |
| 5,642,485 | A | 6/1997 | Deaton et al. | |
| 5,649,114 | A | 7/1997 | Deaton et al. | |
| 5,758,328 | A | 5/1998 | Giovannoli | |
| 5,774,868 | A | 6/1998 | Cragun et al. | |
| 5,832,457 | A | 11/1998 | O'Brien et al. | |
| 5,857,175 | A | 1/1999 | Day et al. | |
| 5,865,470 | A | 2/1999 | Thompson | |
| 5,866,181 | A | 2/1999 | Hill | |
| 5,887,271 | A | 3/1999 | Powell | |
| 5,892,827 | A | 4/1999 | Beach et al. | |
| 5,895,075 | A | 4/1999 | Edwards | |
| 5,926,795 | A | 7/1999 | Williams | |
| 5,943,654 | A | 8/1999 | Goodwin, III et al. | |
| 5,956,877 | A | 9/1999 | Raasch et al. | |
| 5,974,396 | A | 10/1999 | Anderson et al. | |
| 5,974,399 | A | 10/1999 | Giuliani et al. | |
| 6,009,411 | A | 12/1999 | Kepecs | |
| 6,014,634 | A | 1/2000 | Scroggie et al. | |
| 6,026,370 | A | 2/2000 | Jermyn | |
| 6,026,373 | A | 2/2000 | Goodwin III | |
| 6,041,309 | A | 3/2000 | Laor | |
| 6,042,149 | A | 3/2000 | Roshkoff | |
| 6,047,263 | A | 4/2000 | Goodwin, III | |
| 6,055,573 | A | 4/2000 | Gardenswartz et al. | |
| 6,067,524 | A | 5/2000 | Byerly et al. | |
| 6,076,069 | A | 6/2000 | Laor | |
| 6,138,911 | A | 10/2000 | Fredregill et al. | |
| 6,151,586 | A | 11/2000 | Brown | |
| 6,151,587 | A | 11/2000 | Matthias | |
| 6,240,394 | B1 | 5/2001 | Uecker et al. | |
| 6,278,979 | B1 | 8/2001 | Williams | |
| 6,282,516 | B1 | 8/2001 | Giuliani | |
| 6,304,849 | B1 | 10/2001 | Uecker et al. | |
| 6,307,958 | B1 | 10/2001 | Deaton et al. | |
| 6,321,210 | B1 | 11/2001 | O'Brien et al. | |
| 6,334,108 | B1 | 12/2001 | Deaton et al. | |
| 6,351,735 | B1 | 2/2002 | Deaton et al. | |
| 2003/0205412 | A1 | 11/2003 | Hewitt et al. | |
| 2004/0018330 | A1 * | 1/2004 | McDonald | 428/43 |
| 2004/0211600 | A1 * | 10/2004 | Schuller et al. | 177/25.15 |

FOREIGN PATENT DOCUMENTS

| | | | |
|---|---|---|---|
| EP | 0837411 | A1 | 4/1998 |
| EP | 0853290 | A2 | 7/1998 |
| EP | 1197892 | A2 | 4/2002 |
| FR | 2741987 | | 6/1997 |
| JP | 60193824 | | 10/1985 |
| JP | 63144667 | | 9/1988 |
| JP | 63178875 | | 11/1988 |
| JP | 63191370 | | 12/1988 |
| JP | 3138171 | | 6/1991 |

OTHER PUBLICATIONS

Hobart Food Equipment, "CLA Compact Label Applier", For Trayed Self-Service Meat, Poultry, Fish and Produce, 2 pages, May 1993.

Hobart Food Equipment, "Hilite Label Printer & Applier", For Printing and Applying Merchandising Labels, 2 pages, May 1988.

Hobart Food Equipment, "Ultima 2000 PLU Prepack Weighing System", The Hobart Ultima 2000 PLU Prepack Weighing System Provides Merchandising Flexibility, Nutritional and Text Printing and Is Very Simple To Use, 6 pages, Mar. 1993.

Hobart, "Ultima 2000", The ultimate pre-pack scale/printer merchandising system, 6 pages, Dec. 1992.

Hobart, "Weigh/Wrap/Label Systems", 16 pages, Aug. 1999.

* cited by examiner

LABEL SUPPLY, LABEL HANDLING METHOD AND LABEL PRINTING APPARATUS

TECHNICAL FIELD

The present invention relates generally to in-store devices utilized for printing labels, label structures utilized by such printer mechanisms and label handling techniques for such labels.

BACKGROUND

The perishable foods sections of most supermarkets and grocery stores such as the meat department, bakery, deli and produce department, typically include one or more in-store scales having printers for printing labels with item name, weight or count, and price information. The labels are then applied to the packaged items. Many such printers are provided as part of in-store scales or systems including scales.

Increasingly, in-store equipment such as scales/scale systems may include a communications link for receiving information from sites external to the store. As used herein the term scale system refers to any scale device or any larger device that includes a scale, such as a weigh/wrap machine.

It is known to provide coupon dispensing printers at the point of sale in supermarkets and groceries. Typically such coupon dispensers print coupon or other incentive information on paper stock based upon purchases made or not made by the consumer. Product manufacturers, distributors, advertisers and store operators are continually looking for new and improved ways to market and advertise products within the store. Accordingly, using in-store scales to produce product pricing labels having a detachable coupon part pursuant to the teachings contained in U.S. Patent Publication No. 2004/0211600 A1 provides various advantages. As described in U.S. Patent Publication No. 2004/0211600 A1 in one technique a label output from the scale may have a detachable coupon part with a fold line that allows a coupon bar code to be folded under the label so that the coupon bar code faces downward against a package to which the label is subsequently applied. It would be desirable to provide a label structure, technique and apparatus for facilitating this folding operation.

SUMMARY

In one aspect, a supply of labels for use in pricing products and distributing marketing information includes a liner having a release surface. A plurality of labels are removably attached to the release surface, each label including a product pricing part and a marketing part. At least one separation line is formed between the product pricing part and the marketing part. The marketing part includes a first sub-part and a second sub-part, with a fold line located between the first sub-part and the second sub-part. The fold line and the separation line are respectively configured such that a tendency of the label to fold along the fold line is greater than a tendency of the label to fold along the separation line.

In another aspect, a method of distributing labels involves utilizing a printer having an associated supply of labels of a type having at least one fold line; printing information on a front side of a given label; feeding the printed label out of a label exit opening; and contacting the label so as to cause the label to begin to fold along the label fold line prior to the label completely exiting the exit opening.

In another aspect, a method of distributing labels involves utilizing a printer having an associated supply of labels of a type having at least one fold line, the labels removably attached to a liner; printing information on a front side of a given label; feeding the printed label out of a label exit opening; and contacting the label so as to cause the label to begin to fold along the label fold line prior to the label being removed from the liner.

In a further aspect, a label printing apparatus includes a housing and a label feeding mechanism for moving labels along a label path. A print head is located within the housing for printing indicia on labels traveling along the label path. A label exit opening is provided through which printed labels exit the housing during operation of the label feeding mechanism. A label obstructing member is positioned to the exterior of the label exit opening and located in a label obstructing position such that an exit end portion of a label feeding out from the label exit opening contacts the label obstructing member during feed out.

DESCRIPTION

Figure 1:
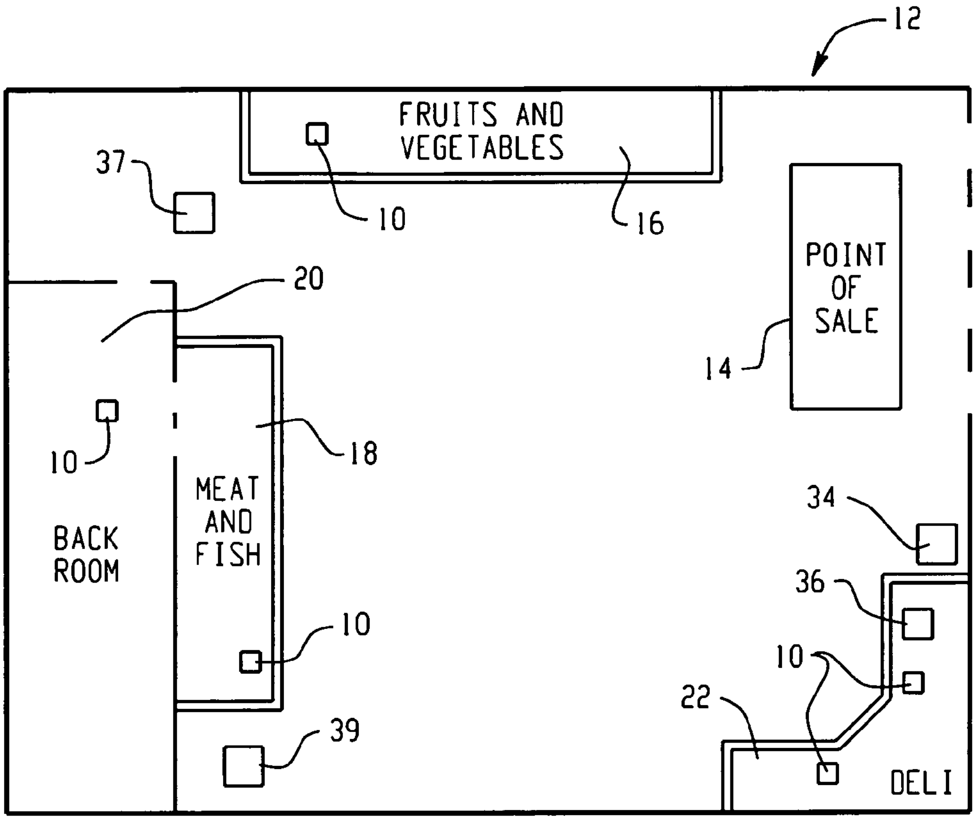
FIG. 1 is a top plan schematic of an exemplary store.

As reflected in FIG. 1, one or more food product scales 10 may be used to provide product pricing labels within a store 12. The store 12 may typically include a point of sale 14 with associated check out scanning terminals. The scale 10 is preferably located at another location, such as a perishables department as represented by the fruit and vegetable department 16, the meat and fish department 18 or associated back room 20, or the deli department 22.

Figure 2:
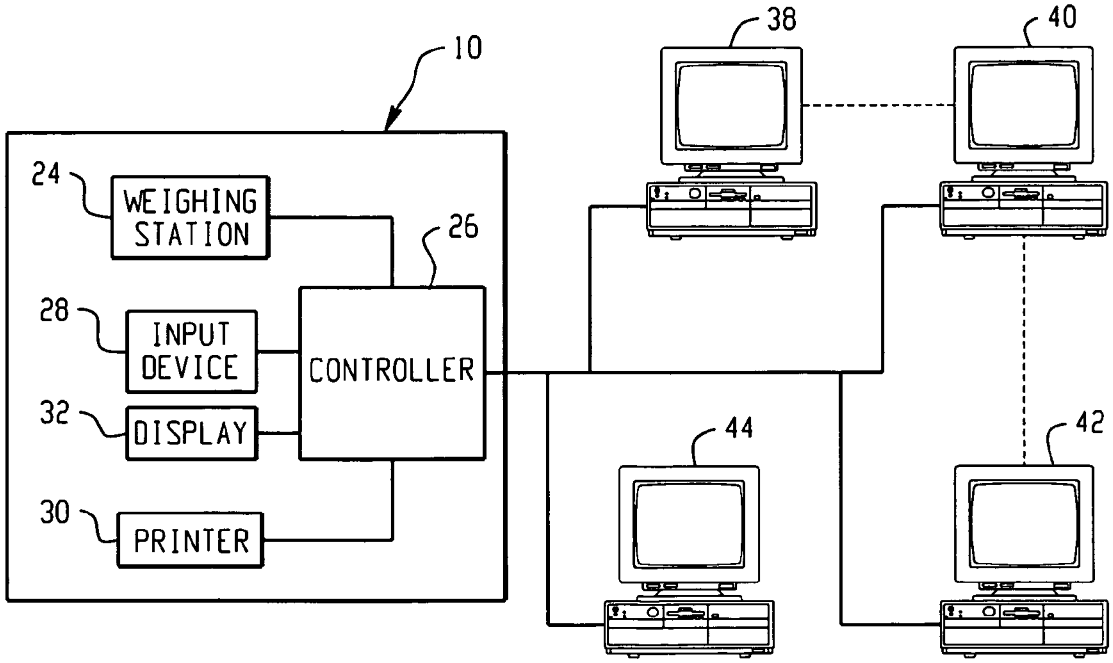
FIG. 2 is a schematic of a scale with communications links to multiple computers/computer systems.

Referring to FIG. 2, the scale 10 includes an associated weighing station 24 having a load cell or other known weighing mechanism or device to produce weight indicative signals that are passed to a processor-based controller 26. A user input device 28 (such as a keypad, a touch sensitive display, a scanner, etc) is also connected to the controller 26. The user input device 28 may be utilized by store personnel (or in the case of a self service situation the customer) to identify the product being weighed, usually by a PLU (price look-up) number. Item identifiers for products being weighed may take other forms as well. For example, the input device could comprise a large number of keys, one for each product that might be weighed. The controller 26 refers to a price database (stored in suitable memory of the controller or accessible via a link to another computer system such as a P.O.S. system or a regional or national computer system of a store chain) to identify the price per unit weight linked to the entered PLU or other product identifier, and calculates a total price for the product based upon the weight as indicated by the weight indicative signals received from the weighing station 24. The controller 26 then establishes product print data (such as total price, price per unit weight, product bar code, logos or other image data, label set-up and format) to be delivered to a printing mechanism 30. The scale 10 may be connected for communication with one or more store or remote computers/computer systems 38, 40, 42, 44 via suitable communication links.

Figure 3:
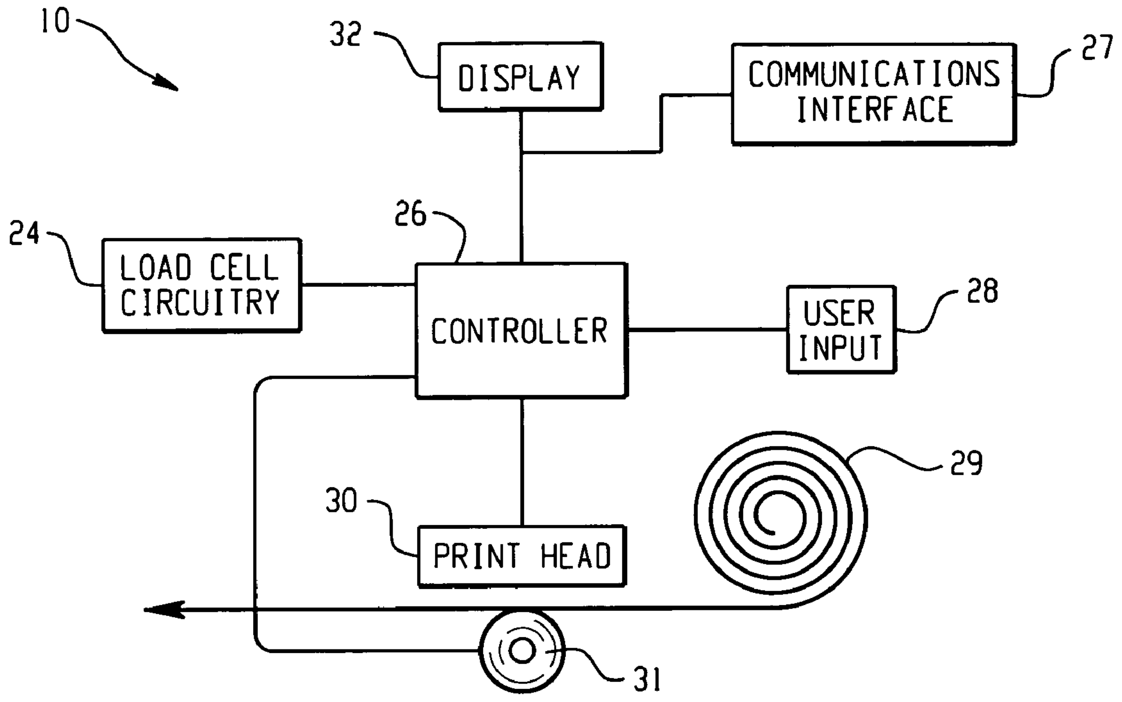
FIG. 3 is a schematic of an exemplary scale including a supply of label stock in the form of a roll.

As seen in FIG. 3, the printing mechanism 30 includes a print head and associated supply of labels 29 to be applied to products. Typically, a print roller 31 opposes the print head and is driven to cause movement of the label stock past the print head 30. However, other variations of label feeding mechanisms could be used. The print head may be a thermal print head, with the labels including a thermally activated layer. However, it is recognized that other print head types and corresponding label types could be used. The adhesive side of the labels may be entirely or partially coated with adhesive. The labels may be formed of any suitable material. The various components of the scale 10 could be integrated into a single housing or unit. Alternatively, the scale 10 may be formed of components formed as separate units and connected together for communication with each other, in which case the controller may be a distributed controller, with various control functions distributed among the components. As used herein the terminology "controller" is intended to encompass the distributed controller configuration. Further, the term "controller" is intended to broadly encompass the collection of circuits, processors and other components that carry out the various operating and processing functions of the scale and its component parts. The scale could also be integrated with a wrapping machine.

Figure 5:
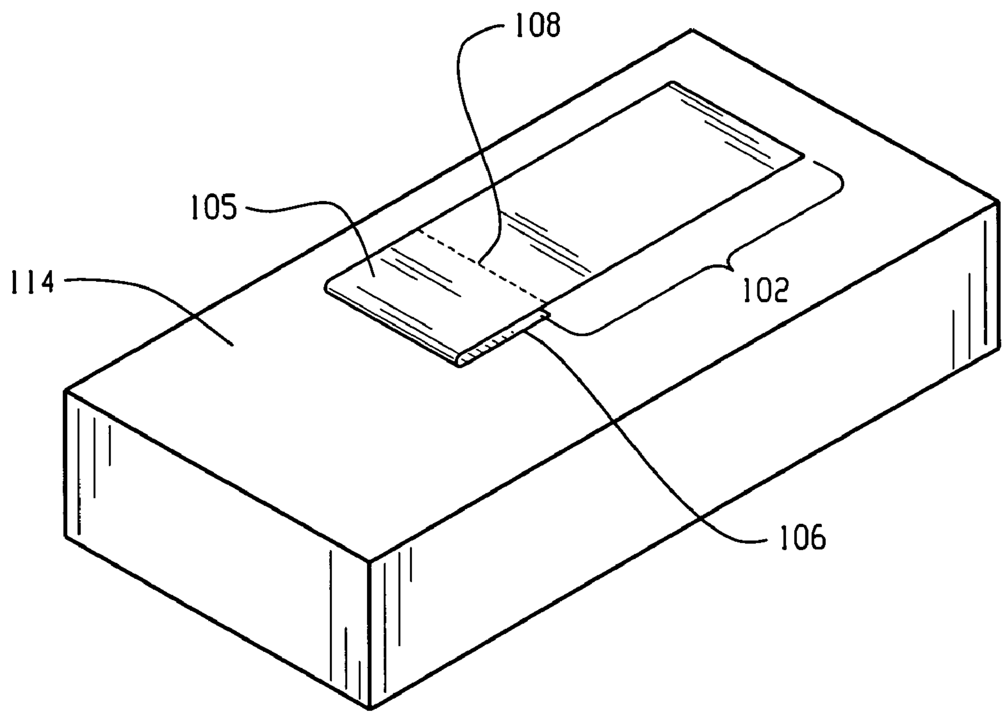
FIG. 5 depicts the label of FIG. 4B applied to a package.
Figure 4A:
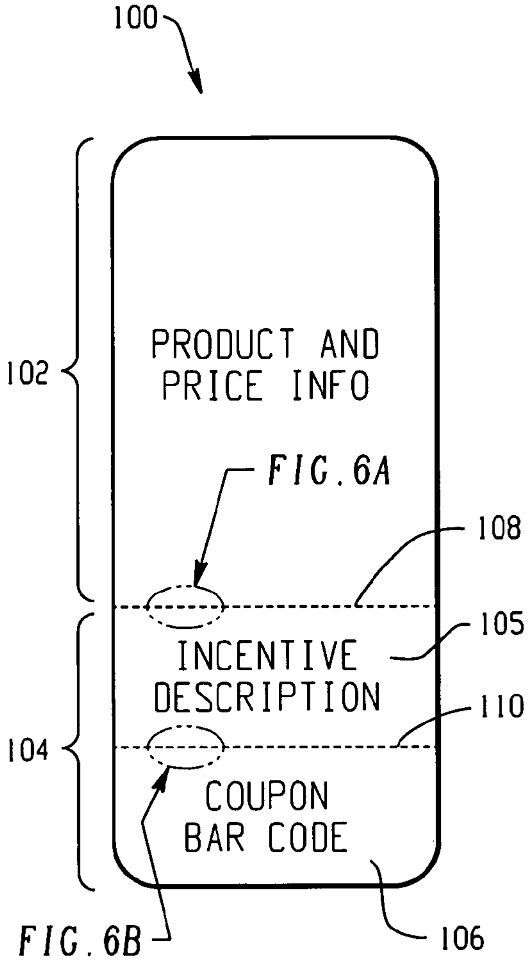
FIGS. 4A and 4B show one embodiment of a label construction.
Figure 4B:
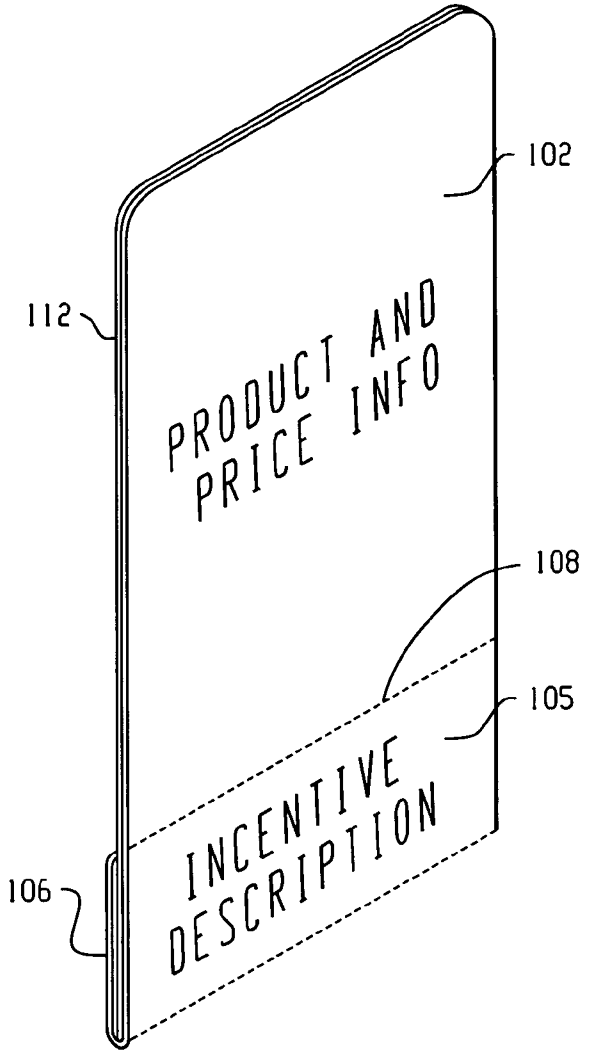

In one embodiment, labels used in such a scale may take the form of that depicted in FIGS. 4A and 4B. FIG. 4A shows an upper, printing surface of a label 100 having parts or regions 102 and 104. A separation line 108, which by way of example may be a series of perforations or a score line in the label, divides part 102 from part 104. A fold line 110 divides part 104 into sub-parts 105 and 106. It is contemplated that an entirety of the rear surface of the label would include an adhesive layer, although less than the entirety of the surface could be adhesive. By way of example, the label 100 can be used in connection with scale label incentives as follows. When a product is weighed and the price of the product calculated, the printing mechanism prints price and product information, which may include a pricing bar code, on part 102. If the weighed product includes an incentive link (as described in U.S. Patent Publication No. 2004/0211600 A1), the printing mechanism prints incentive information on one or both of sub-parts 105 and 106. In one example, indicia identifying the nature of the incentive to the customer is printed on sub-part 105, and a coupon bar code is printed on sub-part 106. The label sub-part 106 is folded under the label sub-part 105 to produce a folded label as shown in the perspective of FIG. 4B where the adhesive layer 112 is illustrated for ease of understanding. The folded label can then be applied to a package 114 per FIG. 5 to produce a labeled package assembly. In the illustrated embodiment label sub-parts 105 and 106 are of similar size. When sub-part 106 is folded under and against sub-part 105 it becomes adhesively attached thereto with the coupon bar code facing the opposite direction of the incentive description. When the folded label is applied to package 114, only label part 102 is adhesively held to the package because the adhesive on sub-parts 105 and/or 106 is no longer exposed. This construction enables the incentive portion of the label 100, comprised of sub-parts 105 and 106, to be removed from the package for use by a customer by separation along line 108. Alternatively, if the customer chooses not to use the incentive, the coupon bar code is left adjacent to and facing the package so that it will not interfere with any scanning operation at the checkout location of the store. In the case of weighed products not having incentive links, various types of other information could be printed on one or both of sub-parts 105 and 106 to communicate with the consumer, including marketing information, other non-coupon advertising information, cooking instructions for the weighed product, health tip information or dietary information. Even where the label sub-parts 105 and 106 are not used for coupon purposes, the folded label configuration may facilitate the inclusion of more information on the label while at the same time enabling the footprint of the label as applied to the package to remain relatively manageable.

Figure 13:
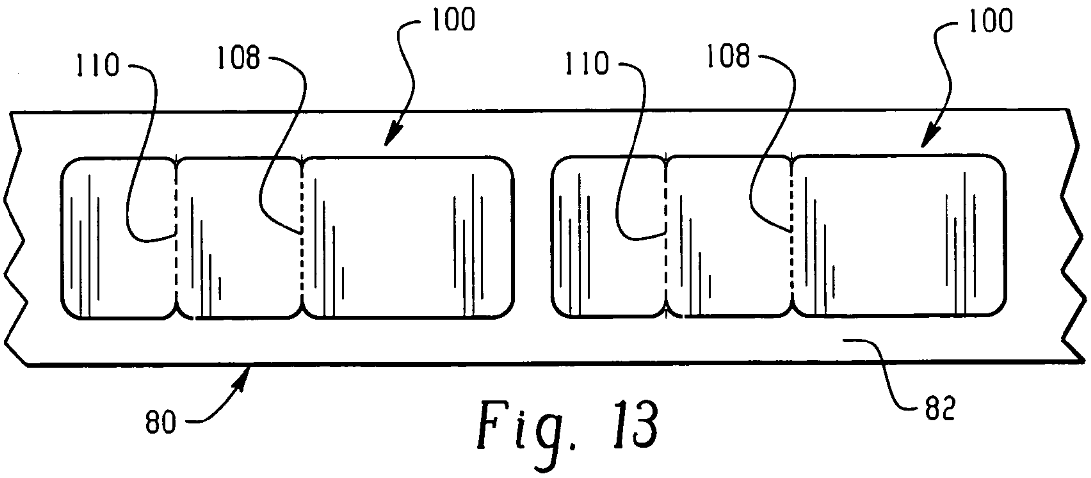
FIG. 13 depicts a partial top view of labels removably attached to a release surface of a liner.

Referring to FIG. 13, the label supply 29 may be formed by a liner or backing material 80 having a release surface 82, with multiple labels 100 removably attached to the release surface, adhesive sides down against the release surface 82. The liner 80 with attached labels 100 may be formed in a roll as shown schematically in FIG. 3. In other variations the label supply 29 could be formed from linerless label stock.

Figure 6A:
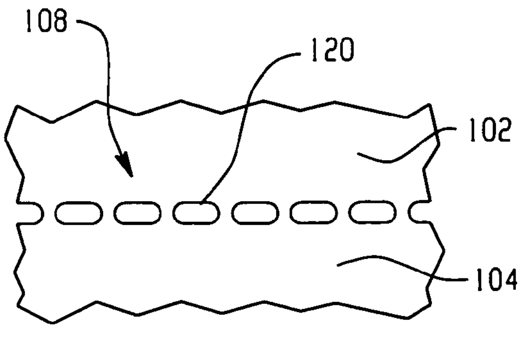
FIGS. 6A and 6B show enlarged views of the respective regions of FIG. 4A.
Figure 6B:
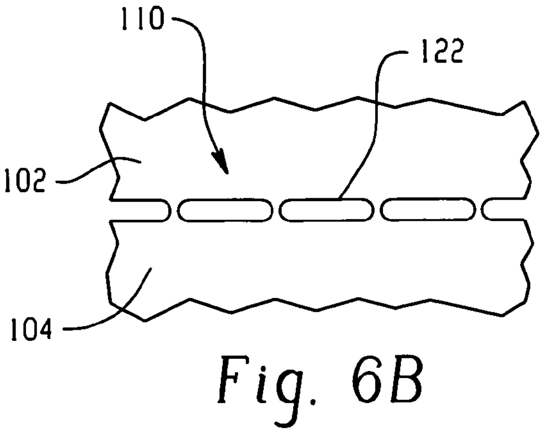

Considering the label configuration reflected in FIGS. 4A and 4B, applicants have identified an advantageous label construction that facilitates the desired folding operation. Specifically, and referring to FIGS. 6A and 6B showing enlarged partial views of the separation line 108 and the fold line 110 respectively, the separation line 108 and the fold line 110 are respectively configured such that a tendency of the label to fold along the fold line 110 is greater than a tendency of the label to fold along the separation line 108. As illustrated, the separation line 108 is a line of perforations 120 and the fold line 110 is a line of perforations 122. A degree of attachment between label part 102 and label part 104 along the separation line 108 is greater than a degree of attachment between the sub-part 105 and the sub-part 106 along the fold line 110. In one example, the degree of attachment between the label part 102 and the label part 104 along the separation line 108 is greater than about 30%, the degree of attachment between the sub-part 105 and the sub-part 106 along the fold line 110 is less than about 20%, but variations on degrees of attachment are possible. Moreover, other techniques may be used to provide a label that has a greater tendency to fold along a fold line than along a separation line. For example, scoring may be used to form the respective lines and the degree or depth of scoring on the fold line could be greater than along the separation line. It is also possible that one line could be a score line and the other line a line of perforations.

Figure 7:
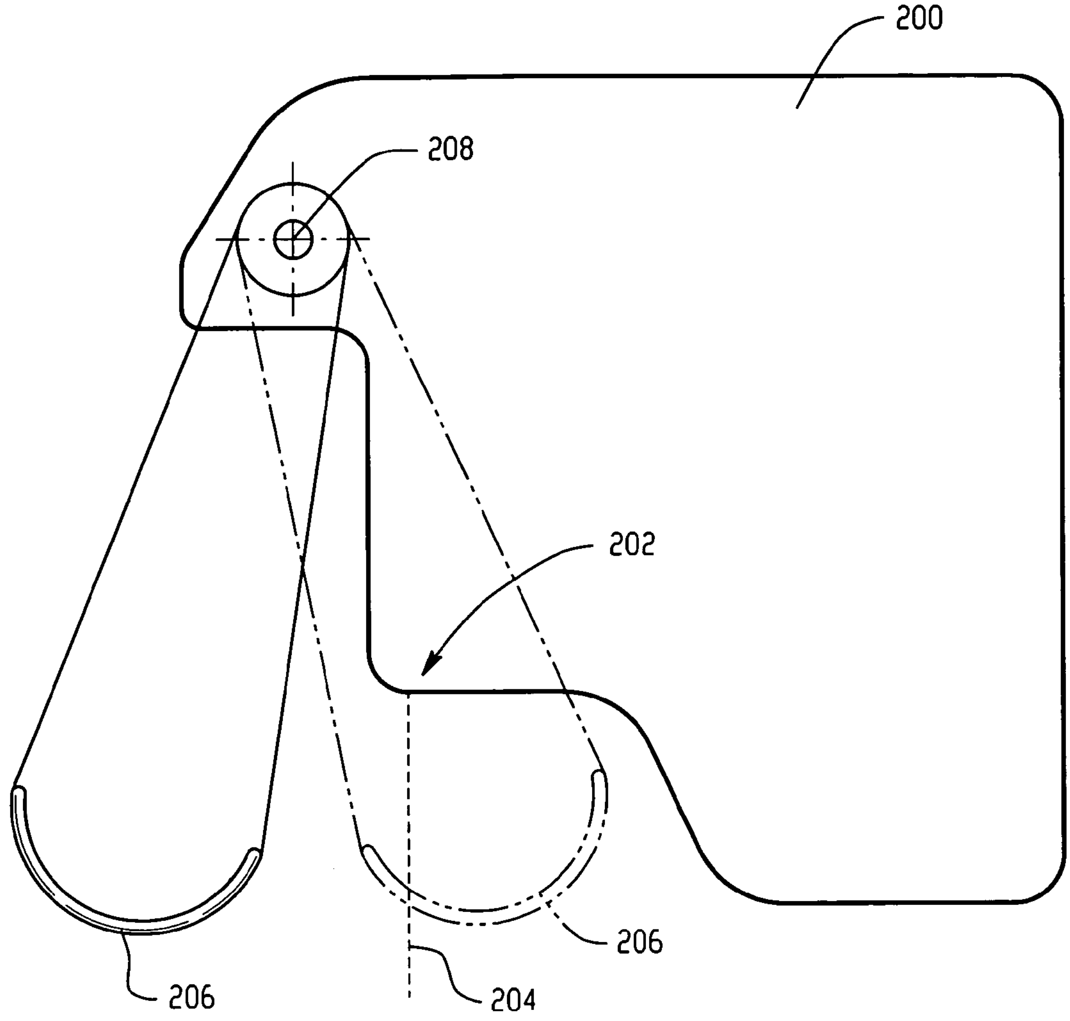
FIG. 7 is a schematic depiction of a scale or other printer mechanism with a movable label obstructing member.
Figure 8D:
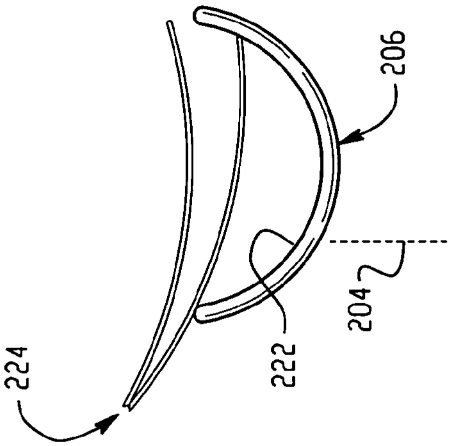
FIGS. 8A-8D show the progressive folding of a label as it contacts the label obstructing member.
Figure 8C:
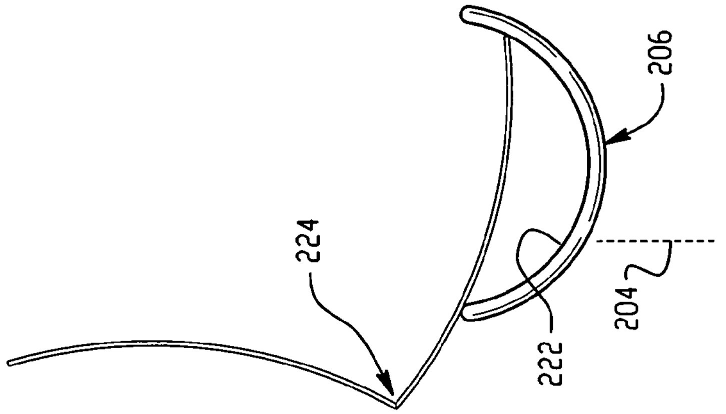
Figure 8B:
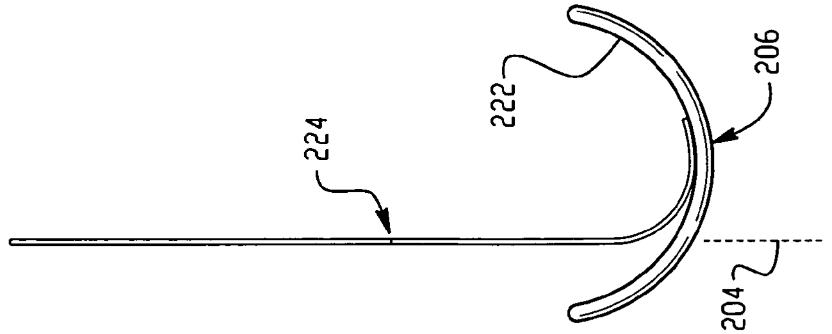
Figure 8A:
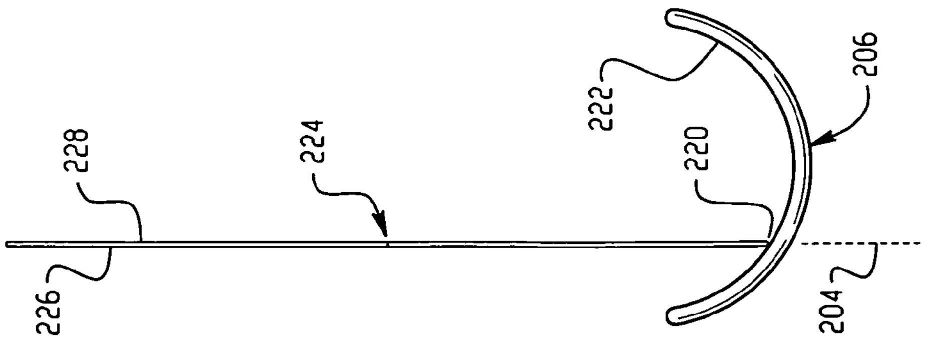

Referring now to the schematic diagram shown in FIG. 7, one embodiment of an apparatus adapted to facilitate folding of a label as it is output from a scale or other printer is shown. The scale 200 includes a label exit opening 202 through which printed labels are fed enabling them to be removed by a scale operator and applied to a package. A normal output path for labels is shown by dashed line 204. A label obstructing member 206 is positioned to the exterior of the label exit opening 202. In the illustrated embodiment the member 206 is connected for movement about a pivot axis 208 by a rotary solenoid 210 or other actuator allowing the member 206 to be selectively moved between a label obstructing position (e.g., the right hand position in FIG. 6) and a non-label obstructing position (e.g., the left hand position in FIG. 6) based upon whether it is desired to fold the label that is being output by the scale. When located in the label obstructing position, an exit end portion of a label feeding out from the label exit opening 202 contacts the label obstructing member 206 prior to completion of feed out of the label from the label exit opening 202. Referring specifically to the series of top, schematic views shown in FIGS. 8A-8D, an exit end 220 of a label contacts a curved surface 222 of member 206 and continued movement of the label along path 204 is obstructed causing the label to begin to follow the curved surface 222 as shown in FIG. 8B. The location of a fold line in the label is shown at 224. The front side of the label is shown at 226 and the rear, adhesive side of the label is shown at 228. In FIG. 8C the continued progression of the label causes the label to bend along the fold line 224 and the final position of the label is shown in FIG. 8D, at which point the operator can readily grasp the label on opposite sides of the fold line without having to touch the adhesive side 228 of the label. Thus, it is the forces generated by the interaction between the label obstructing member 206 and the label that cause the label to begin to fold. This technique could be used for a label having the configuration of that shown in FIGS. 4A and 4B, or could be used with other label configurations, such as labels that only have one or more fold lines, without any separation lines (e.g., as suggested in FIGS. 4-7 of U.S. Patent Publication No. 2004/0211600 A1).

Figure 9D:
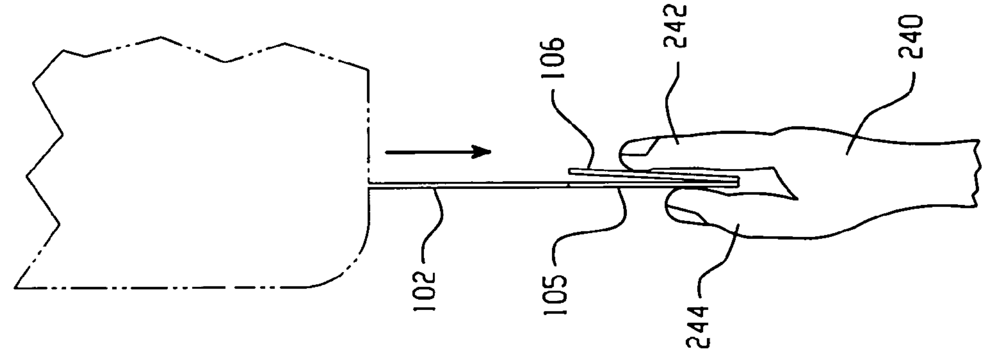
FIGS. 9A-9D depict the progressive folding of a label as it contacts a person's hand during output from a scale or other printer.
Figure 9C:
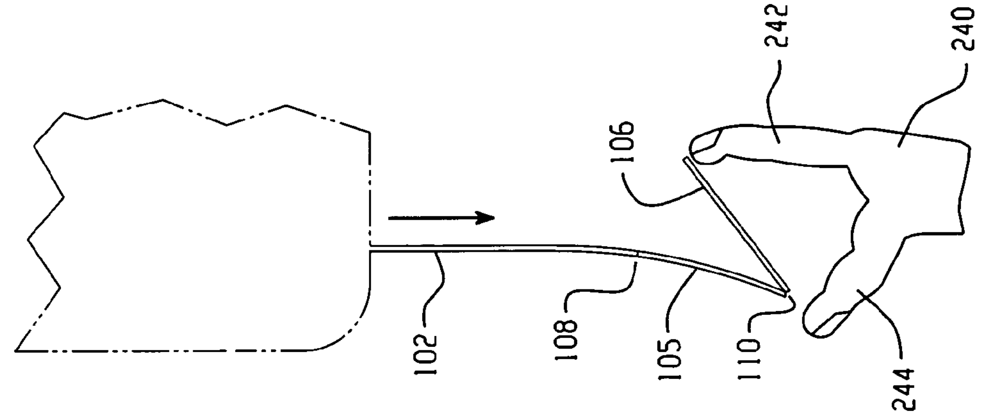
Figure 9B:
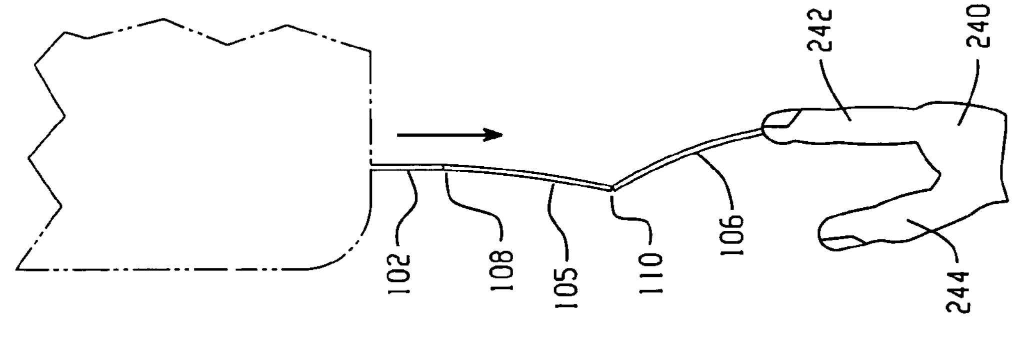
Figure 9A:
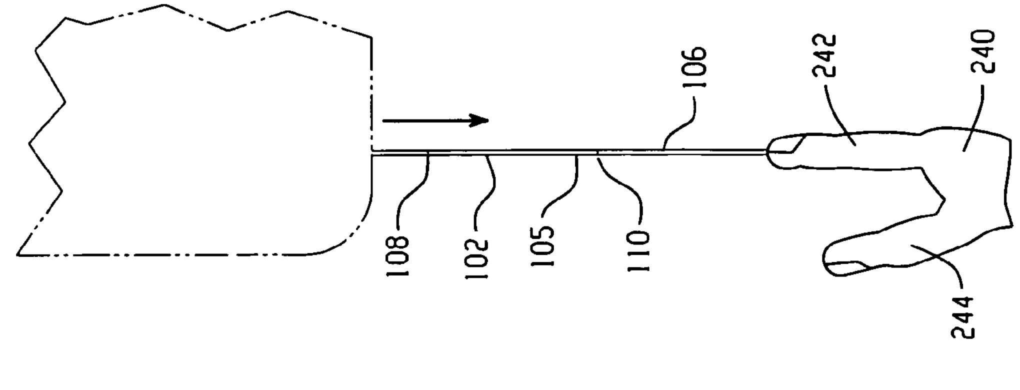

The technique of initiating folding of the label by obstructing the movement of the label as it exits the label opening can also be performed manually. As seen from FIGS. 9A-9D, a scale operator's hand 240 (e.g., by appropriate positioning of a finger or fingers 242 in line with the label path) could be used to obstruct movement of the label as it exits the scale, with the resulting progression of label fold making it a simple matter for the operator to complete the fold by pressing label parts 105 and 106 together between thumb 244 and finger(s) 242 as best seen in FIG. 9D. This type of folding sequence can be achieved in connection with printers that output each printed label in a continuous manner (e.g., without stopping feed-out of the printed label). Alternatively, the printer may be configured to momentarily stop feed out of a printed label, allowing the scale operator to move his/her hand into contact with the protruding end of the label so that the operator can push on the label to initiate the fold. In one example, such a momentary halting of printed label feed out may be for a specific time period (e.g., 0.5 sec, 1.0 sec, 1.5 sec or some other time period determined to be suitable).

Figure 10D:
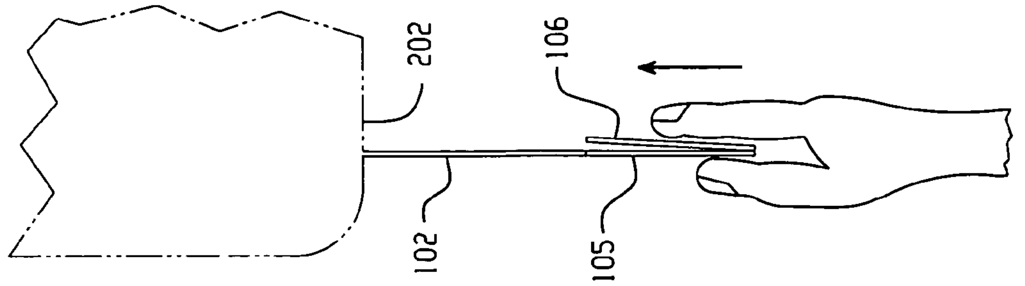
FIGS. 10A-10D depict the progressive folding of a label caused by movement of a person's hand while the label is located to be retrieved from the scale or other printer.
Figure 10C:
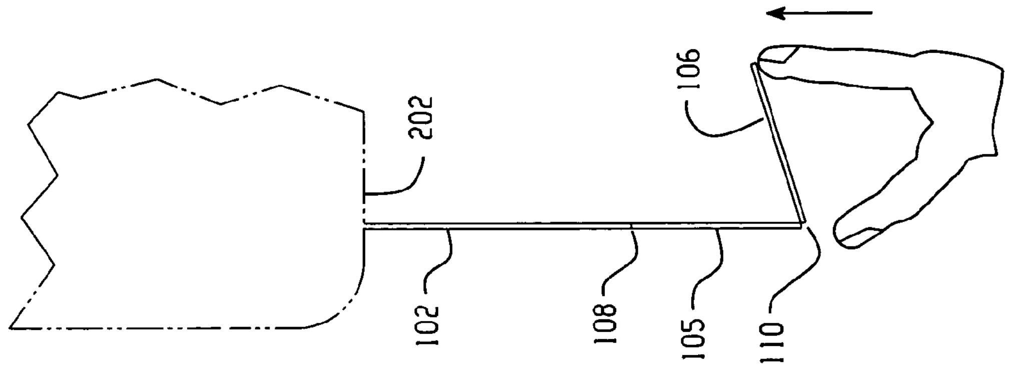
Figure 10B:
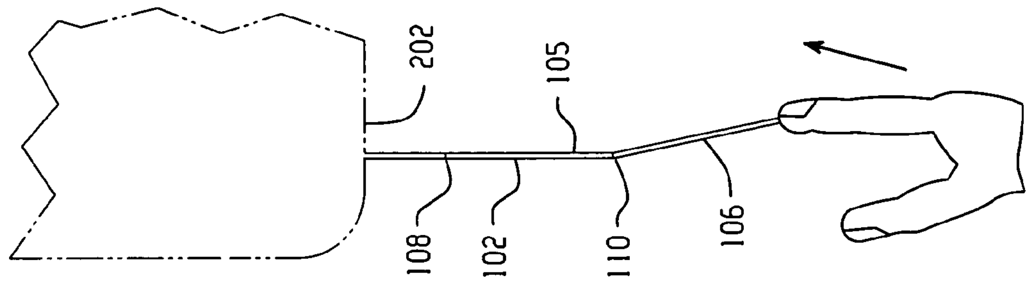
Figure 10A:
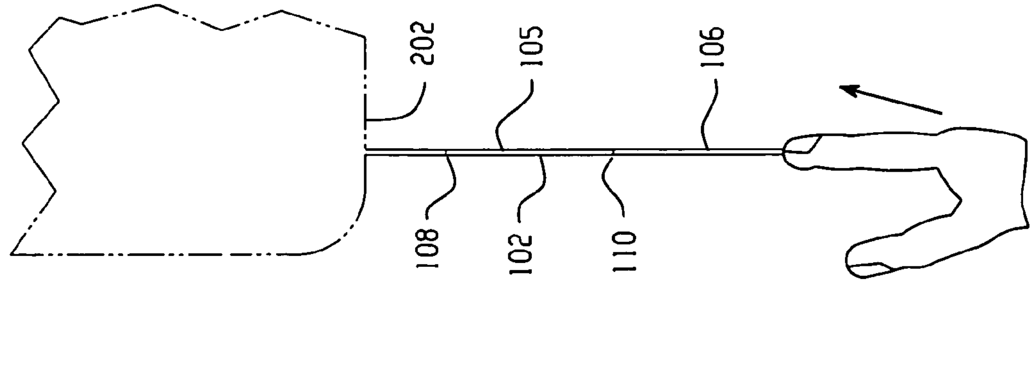

Of course, in some situations the label feed out may be completed without the operator ever having obstructed movement of the label. In those cases, label folding can still be initiated by a single hand of the scale operator. Specifically, at the end of a typical label feed out operation a majority of the label protrudes from the exit opening 202 as shown in FIG. 10A, but the label is supported in that position (e.g., by a small portion of the inner end of the label still being attached to the release surface of the label stock backing) so as to avoid the label dropping to the floor before an operator retrieves the label. When the label is in this position, the operator can move his/her hand 240 into contact with the end of the label and perform a label fold as reflected in the sequence of FIGS. 10B-10D. Thus, this label fold operation takes place prior to the label completely exiting the exit opening 202, but after the feeding operation is completed and the label has been placed in a position for operator retrieval.

Figure 11A:
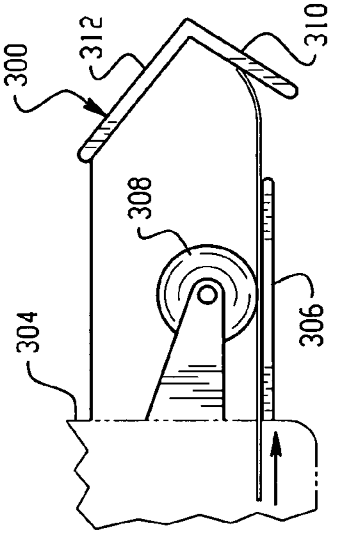
FIGS. 11A-11D depict another embodiment of a printer (as may be associated with a package wrapping machine) including a label obstructing member that causes a label to fold as it is output.
Figure 11B:
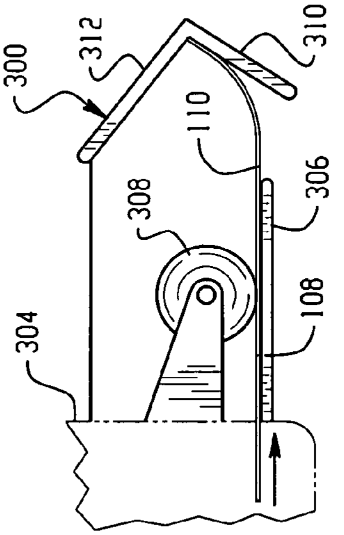
Figure 11C:
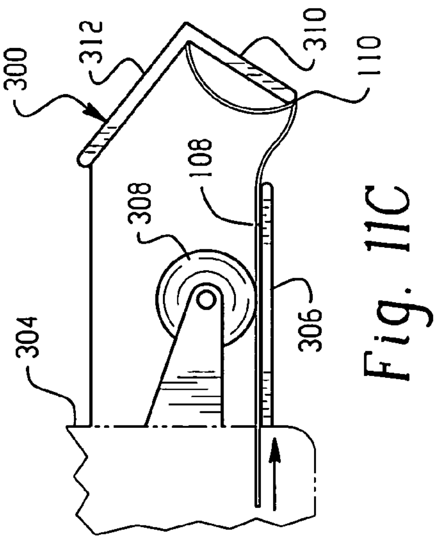
Figure 11D:
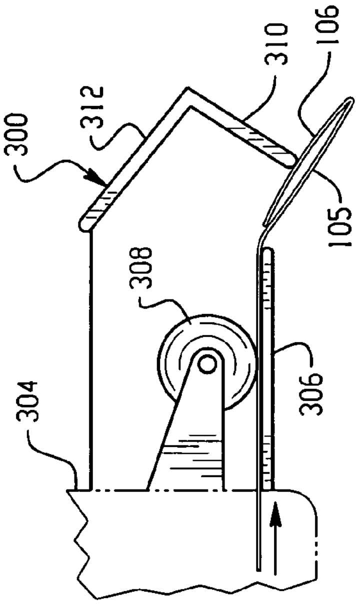
Figure 12:
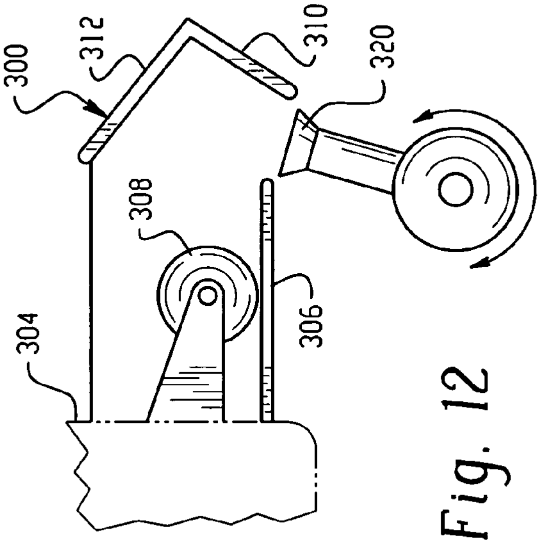
FIG. 12 depicts the printer of FIG. 11 including a label applying wand.

While much of the description above focuses on scales of the type used by operators, where operators manually apply printed labels to packages, it is recognized that scales may also be integrated into more complex machinery, such as wrapping machines that automatically weigh, wrap and label trayed food products. Exemplary of such wrapping machines are those described in U.S. Pat. Nos. 5,144,787 and 6,170,236. Various techniques for automatically applying labels to the packages are know in connection with such machines, including those described in U.S. Pat. Nos. 5,221,405 and 6,595,259. Adaptations to such machines can permit printed labels to be automatically folded and applied to packages. In particular, referring to FIGS. 11A-11D an angled bracket 300 is positioned beyond the exit opening 302 of a label printer 304 associated with a wrapping machine. The angled bracket may be connected to the housing of the printer in a manner that is fixed or that is adjustable. As the label is output it is fed, adhesive side up, along a label support 306 and held against the label support 306 by a roller wheel or wheels 308 having a release coating or surface. As the exiting end of the label contacts the angled surface of bracket arm 310 the end of the label begins to curve upward as shown in FIG. 11A. Continued progression of the label causes the end of the label to move into the intersection point defined between bracket arms 310 and 312 thereby restricting further movement of the end of the label. The end portion of the label begins to curve and the label begins to fold along fold line 110, which fold line then becomes the leading edge of the label and moved beneath the lower end of bracket arm 310 as shown in FIG. 11C. Continued feed out of the label furthers the folding operation as between label parts 106 and 105. The folded label can then be picked up by a vacuum wand 320 (FIG. 12—label not shown) that rotates the label 180 degrees downward and allows a label applying arm to then move the label downward and onto a package as per U.S. Pat. Nos. 5,221,405 and 6,595,259. The final pressing of the label onto the package assures that label parts 105 and 106 are adhesively held together. In the illustrated embodiment, as a general rule bracket arm 310 should be shorter in length than the part of the label being folded (e.g., in this case label part 106). However it is recognized that angled bracket 300 represents only one variation of a suitable label obstructing member configuration, and that many variations are possible.

Although the invention has been described and illustrated in detail it is to be clearly understood that the same is intended by way of illustration and example only and is not intended to be taken by way of limitation. It is recognized that numerous variations exist, including both narrowing and broadening variations of the appended claims.

What is claimed is:

1. A label printing apparatus including a supply of labels for use in pricing products and distributing marketing information, comprising:

a housing;

the supply of labels comprising:

a liner including a release surface;

a plurality of labels removably attached to the release surface, each label including a product pricing part and a marketing part, at least one separation line between the product pricing part and the marketing part, the marketing part includes a first sub-part and a second sub-part, a fold line located between the first sub-part and the second sub-part, wherein the fold line and the separation line are respectively configured such that a tendency of the label to fold along the fold line is greater than a tendency of the label to fold along the separation line;

wherein, for each label, the first sub-part and second sub-part are of similar size and shape, at least one of the first sub-part and the second sub-part has a rear side that is adhesive;

wherein the greater tendency of the label to fold along the fold line than along the separation line causes the label to fold along the fold line to a greater extent than along the separation line in response to an obstruction force to urge the rear side of the at least one of the first sub-part and the second sub-part toward the rear side of the other of the first sub-part and the second sub-part such that an operator can grasp the label on opposite sides of the fold line without touching the rear side that is adhesive;

a label feeding mechanism for moving labels along a label path;

a print head within the housing for printing indicia on labels traveling along the label path;

a label exit opening from which printed labels exit the housing during operation of the label feeding mechanism;

a label obstructing member positioned to the exterior of the label exit opening and located in a label obstructing position such that an exit end portion of a label feeding out from the label exit opening contacts the label obstructing member during feed out, wherein the label obstructing member is movable between the label obstructing position and a non-label obstructing position.

2. The label printing apparatus of claim 1 wherein, for each label, the separation line is a line of perforations and the fold line is a line of perforations, a degree of attachment between the product pricing part and the coupon part along the separation line is greater than a degree of attachment between the first sub-part and the second sub-part along the fold line.

3. The label printing apparatus of claim 2 wherein the degree of attachment between the product pricing part and the marketing part along the separation line is greater than about 30%, the degree of attachment between the first sub-part and the second sub-part along the separation line is less than about 20%.

4. The label printing apparatus of claim 1 wherein, for each label, the separation line is a score line and the fold line is a score line, the degree of scoring along the separation line is less than the degree of scoring along the fold line.

5. The label printing apparatus of claim 4 wherein, for each label, the separation line is one of a line of perforations and a score line and the fold line is the other of a line of perforations and a score line.

6. The label printing apparatus of claim 1 wherein the label obstructing member includes a curved surface.

7. The label printing apparatus of claim 1 wherein the supply of labels is loaded such that the marketing part exits the label exit opening prior to the product pricing part.

8. The label printing apparatus of claim 7 wherein the second sub-part of a label feeding out from the label exit opening is folded under the first sub-part due to contact with the label obstructing member.

9. A label printing apparatus including a supply of labels for use in pricing products and distributing marketing information, comprising:

a housing;

a supply of labels comprising:

a liner including a release surface;

a plurality of labels removably attached to the release surface, each label including a product pricing part and a marketing part, at least one separation line between the product pricing part and the marketing part, the marketing part includes a first sub-part and a second sub-part, a fold line located between the first sub-part and the second sub-part, wherein the fold line and the separation line are respectively configured such that a tendency of the label to fold along the fold line is greater than a tendency of the label to fold along the separation line;

wherein, for each label, the first sub-part and second sub-part are of similar size and shape, at least one of the first sub-part and the second sub-part has a rear side that is adhesive;

wherein the greater tendency of the label to fold along the fold line than along the separation line causes the label to fold along the fold line to a greater extent than along the separation line in response to an obstruction force to urge the rear side of the at least one of the first sub-part and the second sub-part toward the rear side of the other of the first sub-part and the second sub-part such that an operator can grasp the label on opposite sides of the fold line without touching the rear side that is adhesive;

a label feeding mechanism for moving labels along a label path;

a print head within the housing for printing indicia on labels traveling along the label path;

a label exit opening from which printed labels exit the housing during operation of the label feeding mechanism;

a label obstructing member positioned to the exterior of the label exit opening and located in a label obstructing position such that an exit end portion of a label feeding out from the label exit opening contacts the label obstructing member during feed out, wherein the label obstructing member includes a curved surface.

10. The label printing apparatus of claim 9 wherein, for each label, the separation line is a line of perforations and the fold line is a line of perforations, a degree of attachment between the product pricing part and the coupon part along the separation line is greater than a degree of attachment between the first sub-part and the second sub-part along the fold line.

11. The label printing apparatus of claim 10 wherein the degree of attachment between the product pricing part and the marketing part along the separation line is greater than about 30%, the degree of attachment between the first sub-part and the second sub-part along the separation line is less than about 20%.

12. The label printing apparatus of claim 9 wherein, for each label, the separation line is a score line and the fold line is a score line, the degree of scoring along the separation line is less than the degree of scoring along the fold line.

13. The label printing apparatus of claim 12 wherein, for each label, the separation line is one of a line of perforations and a score line and the fold line is the other of a line of perforations and a score line.

14. The label printing apparatus of claim 9 wherein the supply of labels is loaded such that the marketing part exits the label exit opening prior to the product pricing part.

15. The label printing apparatus of claim 14 wherein the second sub-part of a label feeding out from the label exit opening is folded under the first sub-part due to contact with the label obstructing member.

* * * * *